United States Patent [19]

Crump et al.

[11] Patent Number: 5,549,104

[45] Date of Patent: Aug. 27, 1996

[54] AIR DELIVERY AND EXHALATION EXHAUST SYSTEM FOR PROTECTIVE HELMETS

[75] Inventors: Kevin E. Crump, Winchester; Jimmie D. Gard, Sadieville; Richard A. Oleson, Lexington, all of Ky.

[73] Assignee: E. D. Bullard Company, Cynthiana, Ky.

[21] Appl. No.: 306,932

[22] Filed: Sep. 16, 1994

[51] Int. Cl.⁶ .................................................. A62B 7/10
[52] U.S. Cl. ................... 128/201.25; 128/201.29
[58] Field of Search ................ 128/201.25, 201.29, 128/202.18, 202.19

[56] References Cited

U.S. PATENT DOCUMENTS

| | | | |
|---|---|---|---|
| 645,286 | 3/1900 | Bader | 128/201.23 |
| 1,075,906 | 10/1913 | Duncan et al. | 128/201.23 |
| 1,131,350 | 3/1915 | Engelfried et al. | 128/201.23 |
| 1,148,902 | 8/1915 | Jacobs | 128/201.23 |
| 1,184,785 | 5/1916 | Stern | 128/201.23 |
| 1,872,877 | 8/1932 | Bowers | 128/201.15 |
| 2,377,122 | 5/1945 | Bakke | 128/201.25 |
| 2,529,106 | 11/1950 | Schauweker | 128/201.25 |
| 3,058,463 | 10/1962 | Goodrich, Jr. | 128/863 |
| 3,562,813 | 2/1971 | Origer | 2/410 |
| 4,236,514 | 12/1980 | Moretti | 128/201.23 |
| 4,466,432 | 8/1984 | Wise | 128/201.25 |
| 4,542,538 | 9/1985 | Moretti et al. | 2/438 |
| 5,003,974 | 4/1991 | Mou | 128/201.25 |
| 5,042,474 | 8/1991 | Williamson | 128/201.25 |
| 5,056,512 | 10/1991 | Bower et al. | 128/201.25 |
| 5,133,344 | 7/1992 | Jurrius et al. | 128/201.29 |
| 5,163,185 | 11/1992 | Hodnett | 2/424 |

Primary Examiner—Aaron J. Lewis

[57] ABSTRACT

An air delivery and exhalation exhaust system for a protective helmet such as an abrasive blasting helmet of the type which includes a removably attachable protective body garment is disclosed. The air delivery system may also include a respirator face mask such that the air delivery system forms a first barrier to the introduction of particulate contamination from ambient atmosphere into the helmet and respiratory system of a wearer thereof and the face mask forms a second barrier to such introduction into the respiratory system of the wearer. The air delivery and exhaust system includes an air permeable exhalation exhaust skirt which is open on upper and lower ends thereof, the upper open end of which is removably attachable to and around a lower edge portion of the interior surface of the helmet. The skirt is impermeable to airborne particulate matter such as results from abrasive blasting activities. The system also includes a knitted neck cuff attached to a lower opening defining edge portion of the skirt and a hollow air impermeable, toroid shaped, air circulating collar disposed in and sewn to a lower opening defining end portion of the skirt. The collar contains an air inlet port accessible from outside the skirt to a remote source of breathable air and an air outlet port connectable within the skirt to an air inlet port of the face mask.

37 Claims, 3 Drawing Sheets

AIR DELIVERY AND EXHALATION EXHAUST SYSTEM FOR PROTECTIVE HELMETS

BACKGROUND OF THE INVENTION

This invention relates to a breathable air delivery system for use with a respirator face mask worn under a worker's protective helmet such as an abrasive blasting helmet. The invention also relates to an exhalation exhaust system for use with such a face mask air delivery system and protective helmet, which system also provides a barrier to the introduction of airborne particulate matter into the system and helmet from ambient atmosphere.

Recently enacted regulations of the Occupational Safety and Health Administration ("OSHA") now require workers in abrasive blasting environments to wear a tight fitting respirator face mask under conditions of exposure to atmospheric contaminants which exceed a minimum level. Usually, when an abrasive blasting helmet is worn, a protective garment is also worn to protect the wearer's body from assault by debris from a blasting activity. Such garments, which are typically in the form of a sleeveless poncho, long sleeve parka or the like have an upper open end which is attachable to and around a lower edge portion of the helmet. A typical abrasive blasting helmet contains a dome portion which covers the worker's head and a cowl portion attached to and around a base of the dome portion so as to depend downwardly to cover the worker's face. The cowl portion contains a viewing lens in a frontal portion thereof and a second removable viewing lens in a visor assembly removably attached to the outer surface of a frontal region of the cowl portion. The inner and outer lenses register with one another when the visor is operatively secured to the helmet. By means of this arrangement, the outer lens protects the inner lens from abrasion and can readily be replaced from time to time as necessary.

But when a respirator face mask is worn on a worker's face under the helmet and the protective garment is also worn with the upper open end being attached to and around the helmet, it is important to provide comfortable and convenient means for supplying breathable compressed air directly to the face mask through or under the protective garment from a remote source which will not be contaminated by debris from a blasting operation. It is also important to provide means for readily exhausting exhaled air from the face mask to ambient atmosphere without, at the same time, introducing ambient air with dust or other contaminates therein from the blasting operation into the helmet region around the wearer's face. While abrasive blasting helmets and protective garments which are releasably attachable thereto are, broadly speaking, well known in the prior art, in a preliminary patent search which we have obtained, we have not found any air delivery and exhalation exhaust systems for such an assembly wherein a respirator face mask is also used.

In U.S. Pat. No. 4,455,687 to S. O. G. Johansson dated Jun. 26, 1984 a protective garment is shown having an upper open end attached to and around the base of a safety helmet. Breathable air is supplied into the helmet along a perforated air hose which emits breathable air into the helmet, but no face mask is used and no means for supplying breathable air to a face mask is shown. A detachable collar-like filter fits about the neck of the helmet through which air may be exhausted from the helmet downwardly into the garment. A problem encountered with this system is that breathable air supplied to the helmet is mixed with exhaled air in the helmet and is exhausted through the filter. Obviously, both fresh air and exhaled air will be exhausted through the filter, which is inefficient. Other prior art protective helmets with attached protective garments which have the same shortcoming are disclosed in U.S. Pat. No. 3,911,914 issued to S. O. G. Johansson on Oct. 14, 1975 and U.S. Pat. No. 4,172,294 issued to Leon J. Harris on Oct. 30, 1979.

In U.S. Pat. No. 1,095,089 issued to H. G. Dinn on Apr. 28, 1914 a hooded protective garment is disclosed wherein breathable compressed air is supplied to the hood through what could be considered a very loosely fitting shoulder supported air hose collar. Breathable air is released into the lower front portion of the hood under the chin of the wearer by a perforated distributor connected in the front of the collar. In addition to having the same shortcoming as previously explained, the loose collar can not function as a barrier to restrain blast debris from entering the hood through the arm openings and base of the garment.

By means of our invention, these and other difficulties encountered with prior art abrasive blasting helmets and attached protective garments are substantially overcome.

SUMMARY OF THE INVENTION

It is an object of our invention to provide a novel air delivery and exhalation exhaust system for a protective helmet such as an abrasive blasting helmet.

It is also an object of our invention to provide means wherein a worker can wear an abrasive blasting helmet while receiving breathable air through a respirator face mask and exhaust exhaled air through an exhalation exhaust skirt which is part of a breathable air delivery system.

It is yet another object of our invention to provide an air delivery and exhalation exhaust system for use with a protective helmet which also forms a barrier to the introduction of airborne particulate matter into the system and helmet from ambient atmosphere.

Briefly, in accordance with our invention, there is provided an air delivery and exhalation exhaust system for use with a protective helmet. The system includes a respirator face mask having an air inlet connector and exhalation exhaust structure and being wearable by a person wearing a protective helmet. The system also includes means for exhausting air exhaled by the person and expelled from the face mask to ambient atmosphere. The exhausting means is wearable about the neck of the person and is attachable to the helmet to form, in cooperation with the helmet, a barrier to the introduction of ambient atmosphere containing particulate matter into the helmet, face mask and the respiratory system of the person. The system further includes means located within the barrier for delivering breathable air to the face mask, the delivering means being accessible to a source of breathable air located external to the barrier.

These and other objects, features and advantages of our invention will become apparent to those skilled in the art from a study of the following detailed description and attached drawings upon which, by way of example, only a preferred embodiment of our invention is described and shown. Those skilled in the art will appreciate that details of the preferred embodiment can be departed from without departing from the scope of our invention.

DESCRIPTION OF THE PREFERRED EMBODIMENT

Figure 3:
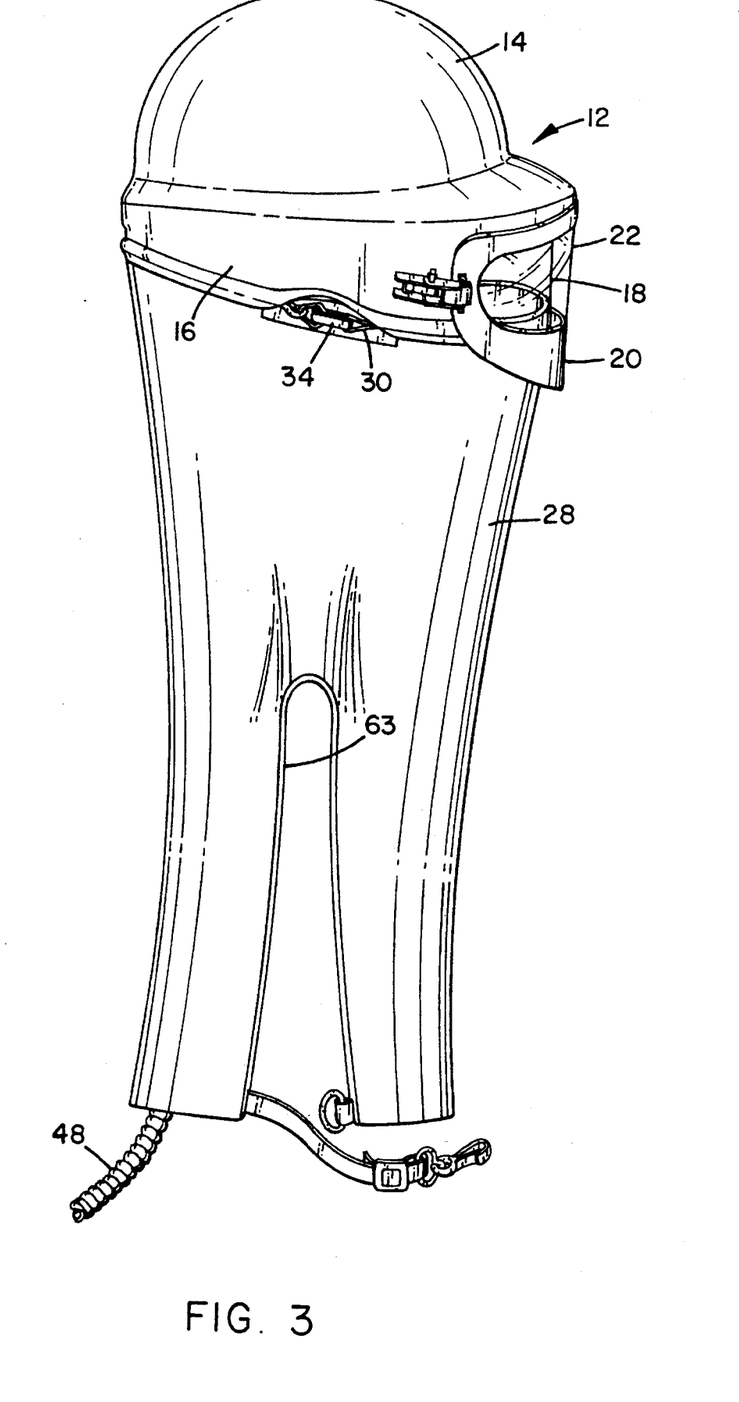
FIG. 3 shows a side elevation view of the helmet, garment and air delivery system of FIGS. 1–2.
Figure 4:
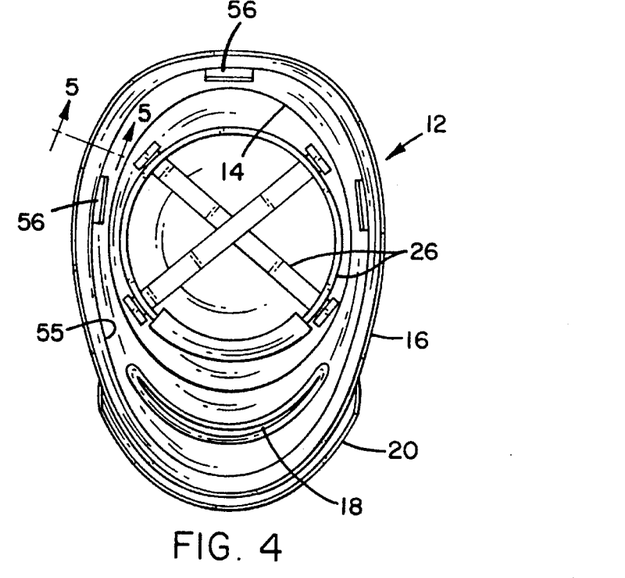
FIG. 4 shows a plan view of the interior of the helmet of FIGS. 1–3 with the garment and air delivery system of those figures removed.

Referring now to the drawing figures there is shown, in a preferred embodiment of our invention, an air delivery and exhalation exhaust system, generally designated 10, for an abrasive blasting helmet 12. The helmet 12 may be constructed of a suitable molded plastic and its conventional features include a hemispheric dome portion 14 adapted to cover the head of a person and a cowl portion 16 depending from a base of the dome portion which is adapted to cover the person's face. A frontal region of the cowl portion 16 contains a permanently attached transparent inner viewing lens 18. A removable visor 20 is hingably attached to the cowl portion 16 and contains a replaceable transparent outer viewing cover or lens 22 which fits in registry with the inner lens 18 when the visor 20 is secured against the cowl portion 16 as by means of a latch 24 (See 24a and b in FIG. 1). The dome portion 14 contains a suitable head band and suspension system 26 as shown in FIG. 4. Attached to and around a base portion of the outer surface of the cowl portion 16 is a conventional protective garment 28 which, in the present example, is in the form of a sleeveless poncho as shown best in FIG. 3. An upper open end portion of the garment 28 contains a drawstring or cable 30 which fits in and around an annular, outwardly opening groove 32 (See FIGS. 1 and 5) formed in and around the base portion of the cowl portion 16. A buckle 34 adjoins both ends of the cable 30 so that the latter is in a sufficiently stretched state in the groove 32 to tightly secure the garment 28 to the cowl portion 16 until unfastened to remove the garment 28 from the helmet 12 as desired.

The novel air delivery and exhalation exhaust system 10 of our invention includes a flexible, air permeable exhalation exhaust skirt 36, which is open on upper and lower ends thereof, a stretchable, resilient neck cuff 38 adapted to fit comfortably on the neck of a worker, and a hollow, toroidal shaped air circulating collar 40. The exhaust skirt 36 may be made of any suitable flexible, air permeable material such as, for example, woven nylon sail cloth which has sufficient porosity to permit air and water vapor to pass through it, while being impervious to airborne particulate matter such as occurs in the region of abrasive blasting operations. A suitable material for use in the skirt 36 is the nylon sail cloth manufactured by Fairhaven Textile Corp., 250 Belmont Avenue, Haledon, N.J. 07508, under part number 112253. The neck cuff 38 is similar in form and function to the turtle neck of the familiar turtle neck sweater and may be made of wool, polyester, nylon or other knit fabric suitable for such wearing apparel. Preferably, it should be suitably stretchable and resilient to fit a range of neck sizes. But to guard against the effects of permanent stretching of the fabric of the neck cuff 38 due, for example, to long term usage and wear, an elastic band 41 (See FIG. 1) may be sewn therein. An upper open end portion of the neck cuff 38 is sewn or otherwise attached to and around a lower open end portion of the skin 36. The air circulating collar 40 should be made of a flexible, air impermeable material such as, for example, a urethane coated woven nylon sail cloth, the sail cloth being similar to that used in making the skirt 36. The collar 40 is disposed in and around an interior base portion of the skirt 36 and should be sewn or otherwise attached to the latter. It contains an elastic band 42 which permits the collar 40 to fit comfortably, yet securely, about the upper neck of the worker above the neck cuff 38.

Figures 1, 2:
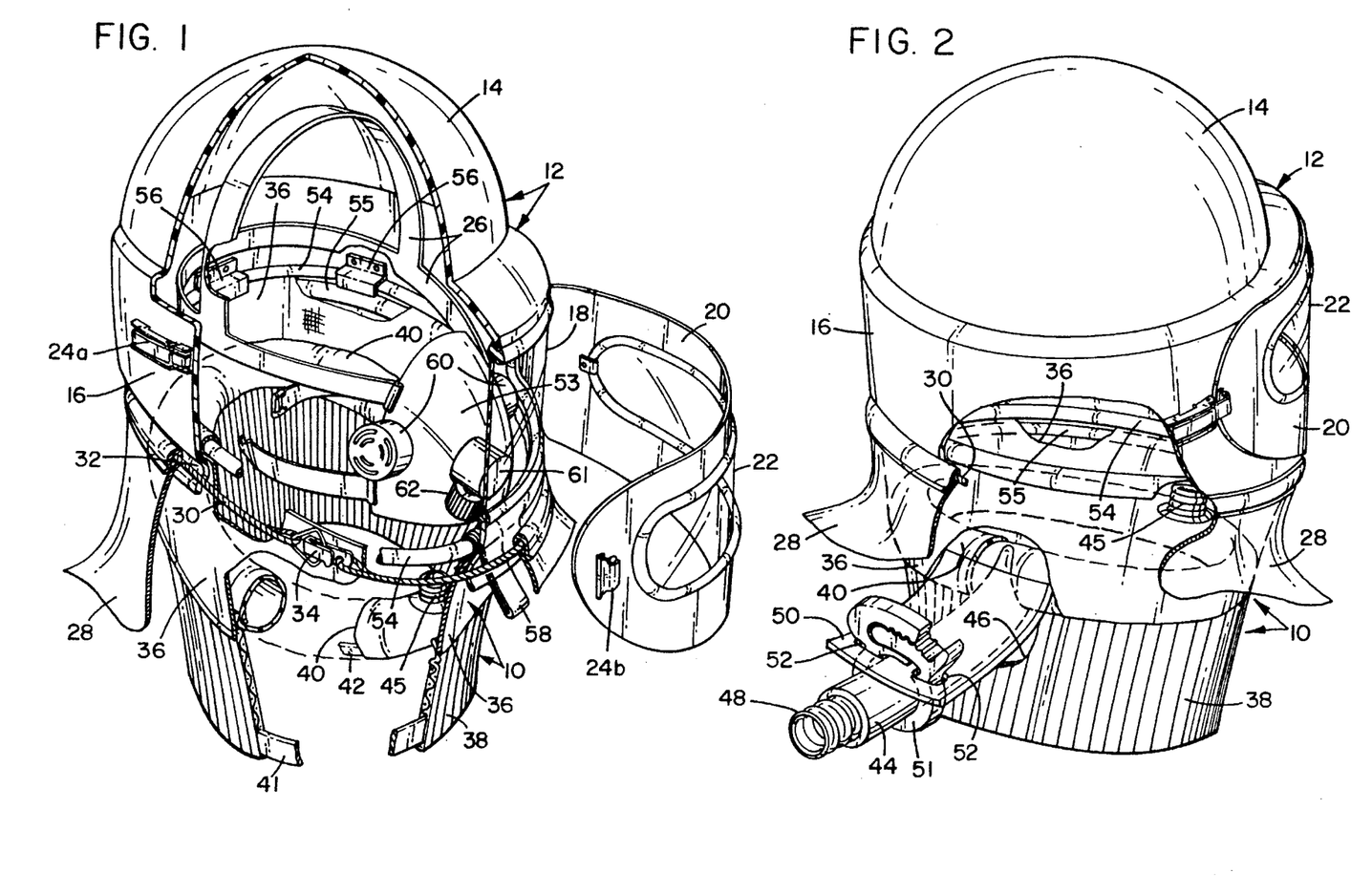
FIG. 1 shows a frontal perspective view of an abrasive blasting helmet having a protective garment and an air delivery system attached thereto with certain portions being torn away for viewing clarity, thus illustrating a preferred embodiment of our invention.
FIG. 2 shows a perspective view of the helmet, garment and air delivery system of FIG. 1 as viewed from the rear thereof, certain portions being torn away for viewing clarity.

The air circulating collar 40 includes an air inlet port which, in the present example, comprises a hollow tube or sleeve 44 of flexible, air impermeable material such as urethane coated, woven nylon sail cloth, the same as the collar 40 to which it is sewn, and an air outlet port 45 comprising an externally threaded face mask hose connector which may be made of a suitable plastic. The hollow interior of the air inlet sleeve 44 communicates with the hollow interior of the collar 40. The sleeve 44 extends from its connection with the collar 40 through a notch 46 (See FIG. 2) formed in an upper edge portion of the collar 38 just below the lower end of the skin 36 where it can be accessed with a conventional breathing tube 48 (See FIG. 2–3) leading from a conventional remote source of breathable compressed air, not shown, up through the back of the garment 28. A rectangularly shaped plastic flap or anchor plate 50 (See FIG. 2) is sewn along one side edge portion thereof between a lower edge of the skirt 36 and an upper edge of the neck cuff 38 so as to overlie a substantial portion of the air inlet sleeve 44. The breathing tube 48 is secured in the sleeve 44 by means of a conventional clamp 51 which encircles the sleeve 44 overlying an end portion of the tube 48. The clamp 51 also contains a pair of interlocking arms which connect to the anchor plate 50 through a pair of openings 52 so as to prevent undue strain on the sleeve 44 when the breathing tube 48 is jerked or pulled. If such a pull were to occur, the clamp 51 will transfer the strain to the anchor plate 50. A suitable example of the clamp 51 is that manufactured by Micro Plastics, Inc., Hwy. 178 North, Flippin, Ark. 72634 and sold as Part No. 22HC1406. The air outlet port 45 is connected directly to an air inlet port 61 of a respirator face mask 53 worn on the face of a person who is also wearing the helmet 12 as shown in FIG. 1.

The face mask 53 of the present example is of conventional type and contains exhalation exhaust structure in the form of a pair of exhalation exhaust valves 60 adapted to direct exhaust air from the mask 53 into the surrounding environment which, in the present example, is contained within the helmet 12 and skirt 36. Specifically, the air inlet port 61 which includes a downwardly projecting interiorally threaded screw connector 62 which is sized to screw onto the exteriorally threaded air outlet connector 45 on the underlying collar 40. In FIG. 1 the face mask 53 and its associated head band and straps 26 is exploded upwardly within the helmet 12 for viewing clarity such that the face mask screw connector 62 and the collar air outlet connector 45 are shown as spaced apart and unconnected. Nevertheless, in the operative state, when the mask 53 and helmet 12 are worn by a person, the screw connector 62 is connected to the connector 45 to supply breathable air directly from the collar 40 to the face mask 53. A suitable example of the face mask 53 is that distributed by E. D. Bullard Company, 1898 Safety Way, Cynthiana, Ky. 41031 and sold as Part No. LMM. The screw connector 62 can be obtained from the same corporation as Part No. LMCON and can be readily fitted by hand onto the inlet port of the exemplified face mask 53.

Figure 5:
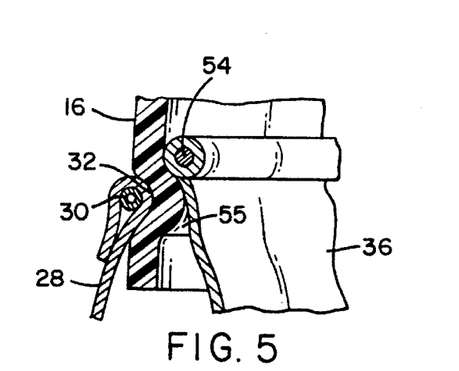
FIG. 5 shows a cross-sectional view of a fragment of the helmet of FIGS. 1–4 as viewed along cross-section lines 5—5 of the latter mentioned figure with fragments of the garment and air delivery system of FIGS. 1–3 replaced.
Figure 6:
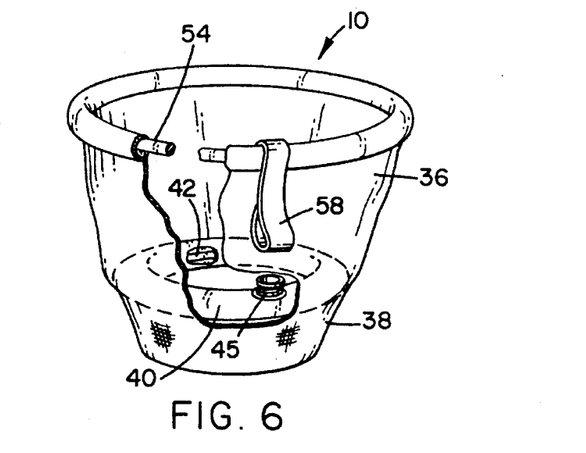
FIG. 6 shows a perspective view of the air delivery system of FIGS. 1–3 and 5.
Figure 7:
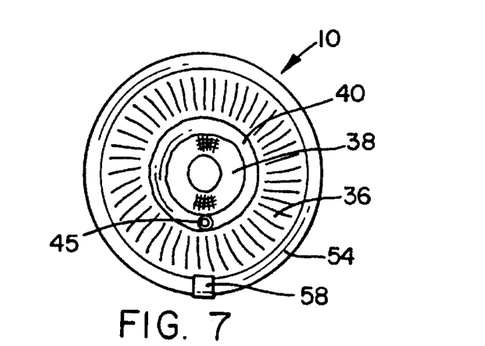
FIG. 7 shows a plan view of the air delivery system of FIGS. 1–3 and 5–6.

The upper open end of the skirt 36 is adapted to removably connect to and around a base edge portion of the interior surface of the helmet 12. In the present example, this is accomplished by means of a resiliently deformable circular tube or hoop 54 which is sewn within a flap formed on and around the upper open end of the skin 36. The circular hoop 54 may be constructed of a suitable plastic such that it can be easily deformed by hand so as to conform to the generally elliptical shape of the interior surface of the cowl portion 16 near the lower edge thereof and, yet, be sufficiently resilient to spring back to its undeformed circular shape when removed from the helmet 12. An endless raised rib 55 is formed on and around a lower edge portion of the interior surface of the cowl portion 16. The rib 55 is disposed on the interior surface of the helmet 12 opposite the outwardly opening groove 32 formed in an exterior surface portion of the cowl portion 16, as best shown in FIG. 5.

To attach the air delivery and exhaust system 10 to the helmet 12, the hoop 54 is held with both hands and manually deformed slightly into a generally elliptical pattern, whereupon one end portion of the ellipse is inserted into the rear of the cowl portion 16 just above and past the rib 55. At the rear of the helmet 12 there are three downwardly opening L-shaped brackets 56 attached to the interior surface thereof (See FIGS. 1 and 4). The brackets 56 are rotationally spaced apart from one another and are located just above the level of the rib 55 such that one end portion of the hoop 54, deformed as aforesaid, will seat therein just above and immediately next to the rib 55. The brackets 56 thus assure that the hoop 54, when seated therein, will remain in a stable position in the helmet 12 just above and next to the rib 55 and will not tend to ride up or tilt along the interior surface of the cowl portion 16. After one end portion of the hoop 54 is seated in the brackets 56, the remaining portion of the hoop 54 is manually pushed over the rib 55 into the cowl portion 16 where it will snap securely into place. Because the hoop 54 is in a deformed condition while so disposed in the helmet 12, it will tend to bear outwardly against and conform to the generally elliptical shape of the cowl portion 16. The endless raised rib 55 then located immediately below the hoop 54 will restrain the hoop 54 from falling out of the helmet 12. Those skilled in the art will appreciate that the three brackets 56 of this example could be reduced to two such brackets or even a single bracket of sufficient width and arcuate shape to conform to the interior curve surface at the rear of the cowl portion 16. In the alternative, a continuous downwardly opening L-shaped channel could be molded so as to be integral with interior curved surface at the rear of the cowl portion 16 at the same level as the brackets 56 of the present example.

To remove the air delivery system 10 from attachment to the helmet 12, a strap 58, one end of which is sewn to an upper end portion of the skirt 36 substantially around the hoop 54 and the other end of which hangs downwardly outside of the skirt 36, is pulled or yanked downwardly by hand such that a front end portion of the deformed hoop 54 is pulled over the rib 55 and downwardly out of the bottom of the cowl portion 16. Since the hoop 54 is resilient, it will then tend to spring back to its undeformed circular condition which will cause the remaining rearward portion of the elliptically deformed hoop 54 to snap out of the brackets 56, over the rib 55 and out of the helmet 12. If for some reason the remainder of the hoop 54 should be hung up or caught in the brackets 56 or above the rib 55 after a frontal portion has been pulled out of the helmet 12 by the strap 58, the wearer can remove the remainder of the hoop 54 simply by placing his hands on opposite sides of the frontal portion of the hoop 54 which is exposed below the rib 55 and cowl portion 16, and work his hands rearwardly between the hoop 54 and a lower edge of the cowl portion 16 to free the remainder of the hoop 54 from the helmet 12.

To apply the helmet 12, air delivery system 10 and garment 28, the base of the garment 28 is spread across a table or workbench so that the rim of the upper open end thereof which contains the cable 30 is approximately centered over the rest of the garment 28. The hingable visor 20 of the helmet 12 is opened to expose a frontal portion of the groove 32 which is ordinarily covered when the visor 20 is closed. With the groove 32 entirely exposed, the rim of the upper open end of the garment 28 is eased over and around the edge of the cowl portion 16 until the cable 30 lies within the groove 32 such that the buckle 34 is approximately at the side of the helmet 12. Making sure that the cable 30 entirely fits within the groove 32 around the base of the helmet 12, the buckle 34 is secured, thus attaching the garment 28 to and around the cowl portion 16. The visor 20 is then closed and locked against the cowl portion 16.

Next, the breathing tube 48 is inserted into the air inlet sleeve 44 of the air delivery system 10 and the clamp 51 is applied over the sleeve 44 and an end portion of the tube 48 and the two end members of the clamp 51 are inserted through the two holes 52 in the anchor plate 50 and interlocked together. A gentle tug of the breathing tube 48 will confirm that it is securely connected within the sleeve 44 and that the anchor plate 50, rather than the sleeve 44, is taking the strain of the tug. With the breathing tube 48 attached to the sleeve 44, the air delivery system 10 is slipped over the wearer's head and the neck cuff 38 is gently straightened on the neck and pulled upward toward the chin such that the air outlet connector 45 on the collar 40 is in front of the wearer's face. A suitable external air supply for supplying air to the breathing tube 48 and collar 40 is then activated and adjusted for adequate air flow in the conventional manner.

Next, the face mask 53 is placed over the mouth and nose of the wearer and the face mask head straps are adjusted to fit the head of the wearer such that mask will provide an air tight fit to the face. To verify air tightness of the fit, a finger may be used to close off the bottom open end of an air inlet connector 61 of the face mask 53 inside the screw connector 62, whereupon the wearer should inhale until the flexible portions of the mask 53 collapse inward slightly due to the resulting negative pressure in the mask and hold his breath for a short time, say, about 5 seconds. If the flexible portions of the mask 53 do not collapse because of air leakage into the mask, or if, during the short time that the wearer's breath is being held, there is air leakage around the edges of the mask, the seal of the mask against the wearer's face is insufficient, whereby further adjustment of the face mask straps will be required, followed by another air leakage test until proper fitting of the face mask 53 is obtained.

Next, the interiorly threaded screw connector 62 on the base of the air inlet connector 61 is threaded onto the exteriorly threaded air outlet connector 45 of the collar 40 with final adjustment of the collar 40 and neck cuff 38 being made as necessary. Finally, with air flowing to the face mask 53 from the collar 40, the helmet 12, with the garment 28 attached, is placed over the wearer's head and the garment 28 is, for the time being, left gathered above and around the helmet 12 and is not pulled down over and around the wearer's body. Thereafter, with his hands, the worker grasps the hoop 54 on opposite sides of his head and slightly compresses the same into an elliptical shape until he can tilt a rear end portion of the hoop 54 into a rear end portion of the cowl portion 16 over the rib 55 and insert the hoop 54 into the brackets 56. Thereafter, the wearer pushes the remaining side and frontal portions of the hoop 54 upwardly over the rib 55 until the hoop 54 snaps into place above and immediately next to the rib 55 around the interior surface of the cowl portion 16. Finally, the garment 28 is pulled down from around the helmet 12 onto and about the wearer's body and may be zippered and/or buckled as appropriate, whereupon the wearer is now ready to enter the work place to commence abrasive blasting operations or perform other activities in the particulate contaminated environment.

Figure 8:
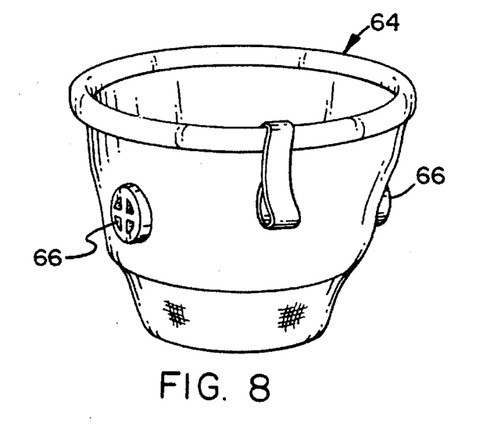
FIG. 8 shows a perspective view of an alternative air delivery system, thus illustrating another embodiment of our invention.

While we prefer to use the air permeable skirt 36 of the present example to serve as both an exhalation exhausting means and a means providing a barrier, in cooperation with the helmet 12, to the introduction of ambient air containing particulate matter into the helmet 12, face mask 53 and the respiratory system of the user, FIG. 8 for example, shows a skirt 64 which is similar to the skirt 36 in all respects except that it is made of an air impermeable material and contains conventional one-way air exhalation valves 66 sewn therein. The valves 66 may be selected to open and thus cause air exhaled by the wearer and expelled from a face mask of the wearer, such as the mask 53 of the previous example, to be released to ambient atmosphere whenever air pressure within the skirt 64 and the helmet of the wearer reach a selected maximum value. This will help to maintain a slight positive pressure within the skirt 64 which is advantageous in keeping particulate matter from finding its way into the skirt 64. On the other hand, the barrier means and exhausting means can also be separate elements as where the skirt 36 is an air impermeable material serving as a barrier to particulate matter and where conventional one-way exhalation valves, such as valves 66 of FIG. 8 are formed in and around the cowl portion 16 of the helmet 12. In such an arrangement, the exhalation exhaust means would be valves in the helmet 12 and the barrier means would be an air impermeable skirt.

While our invention has been described with respect to specific details of a preferred embodiment thereof, it is not intended that such details limit the scope and coverage of this patent other than as specifically set forth in the following claims.

We claim:

1. An air delivery and exhalation exhaust system for use with a protective helmet comprising a respirator face mask having an air inlet connector and exhalation exhaust structure and being wearable by a person wearing a protective helmet, means attachable to said protective helmet and wearable about said person's neck for providing, in cooperation with said protective helmet, a barrier to the introduction of ambient atmosphere containing particulate matter into said protective helmet, face mask and the respiratory system of said person, means for exhausting air exhaled by said person and expelled from said face mask through said barrier providing means to ambient atmosphere, and means located within barrier providing means for delivering breathable air to said face mask, said delivering means being accessible to a source of breathable air located external to said barrier providing means.

2. The system of claim 1 wherein said barrier providing means and said exhausting means comprise a flexible, air permeable exhalation exhaust skirt open on an upper and a lower end thereof, an upper open end portion of said exhaust skirt being attachable to and around a base portion of said protective helmet, and a flexible neck cuff adapted to fit closely about said person's neck, an upper end portion of said neck cuff being attached to a lower open end portion of said exhaust skirt.

3. The system of claim 1 wherein said barrier providing means and said exhausting means comprise a flexible, air impermeable exhalation exhaust skirt open on an upper and lower end thereof, an upper open end portion of said skirt being attachable to and around a base portion of said protective helmet, said exhaust skirt containing at least one exhalation exhaust valve for releasing pressurized air in said protective helmet and exhaust skirt over a selected maximum pressure to ambient atmosphere, and a flexible neck cuff adapted to fit closely about said person's neck, an upper end portion of said neck cuff being attached to a lower open end portion of said exhaust skirt.

4. The system of claim 2 wherein said delivering means comprises a hollow, flexible, air impermeable collar disposed within and around a base portion of said exhaust skirt, said collar including air inlet means accessible from outside of said barrier providing means by a breathing tube connected to a remotely located breathable air source, and air outlet means connectable within said barrier providing means to the air inlet connector of said face mask.

5. The system of claim 1 further comprising a protective helmet, said barrier providing means being removably attachable to and around a base portion of said protective helmet.

6. An air delivery and exhalation exhaust system for a protective helmet comprising a flexible, air permeable exhalation exhaust skirt open on an upper end and a lower end thereof, said exhaust skirt being impermeable to airborne particulate matter which results from abrasive blasting activities, a flexible neck cuff adapted to fit a person's neck, one end of said neck cuff being attached to and around an opening defining lower end portion of said exhaust skirt, a hollow, toroidal shaped air circulating collar constructed of a flexible, air impermeable material disposed in and attached to and around a lower end portion of said exhaust skirt, said air circulating collar including an air inlet port and an air outlet port, and means for removably attaching an opening defining upper end portion of said exhaust skirt to and around a lower edge portion of a protective helmet.

7. The air delivery system of claim 6 wherein said air inlet port comprises a hollow sleeve constructed of an air impermeable material connected on one end thereof to and communicating with a hollow interior of said air circulating collar, said sleeve extending through an opening in said neck cuff for connection of a free end of said sleeve to a breathing tube of a remote source of breathable compressed air.

8. The air delivery system of claim 7 further comprising anchoring means attached to said exhaust skirt and cuff and connectable to said sleeve and to an end portion of a breathing tube when inserted in said sleeve for taking the strain from said sleeve that would otherwise be caused by pulling said breathing tube in a direction tending to dislodge it from said sleeve.

9. The air delivery system of claim 6 wherein said air outlet port comprises an air outlet connector attached to said air circulating collar and communicating with the hollow interior thereof, said air outlet connector being attachable within said exhaust skirt to an air inlet connector of a respirator face mask worn by a person wearing said protective helmet.

10. The air delivery system of claim 6 wherein said air inlet port and said air outlet port are rotationally displaced about 180 degrees from one another on said air circulating collar such that, when said exhaust skirt is attached to said protective helmet such that said air inlet port is positioned facing the back of said protective helmet, said air outlet port will be positioned toward the front of said protective helmet.

11. The air delivery system of claim 6 wherein said exhaust skirt is constructed of woven nylon sail cloth having a porosity sufficient to permit air and water vapor to pass therethrough while being impervious to airborne particulate matter resulting from abrasive blasting activities.

12. The air delivery system of claim 6 wherein said air circulating collar is constructed of urethane coated nylon sail cloth.

13. The air delivery system of claim 6 wherein said removably attaching means comprises a protective helmet including a dome portion for covering the head of a person and a cowl portion attached to and around said dome portion and depending from said dome portion for covering the face of said person, said cowl portion including an elongated, raised rib attached to and extending endlessly about a lower edge portion of an interior surface of said cowl portion, a resiliently deformable circular hoop attached to and around an upper opening defining end portion of said exhaust skirt, said hoop being adapted to snap over said rib and fit in a deformed condition in compression against an interior surface of said cowl portion immediately above said rib such that said rib functions as a barrier to restrain said hoop in said deformed condition and said exhaust skirt from falling out of said protective helmet, and means for pulling a frontal portion of said hoop over said rib and out of a lower end of said cowl portion such that said hoop and exhaust skirt can be removed from attachment to said helmet.

14. The air delivery system of claim 13 wherein said pulling means comprises a flexible strap attached on one end thereof to an upper end portion of said exhaust skirt substantially around said hoop and hanging free outside of said exhaust skirt so that it may be grasped by a person and yanked downwardly to release said hoop and said exhaust skirt from said protective helmet.

15. The air delivery system of claim 13 further comprising bracket means attached to said interior surface on one end portion of said protective helmet for confining a portion of said hoop therein at a level immediately above and next to said rib.

16. The air delivery system of claim 15 wherein said bracket means comprises a plurality of downwardly opening L-shaped brackets rotationally spaced apart and attached to a rear portion of the interior surface of said protective helmet.

17. The air delivery system of claim 16 wherein said plurality is three.

18. The air delivery system of claim 6 further comprising an abrasive blasting helmet, said exhaust skirt being removably attachable to said abrasive blasting helmet to form, in cooperation with said abrasive blasting helmet, a barrier to the introduction of ambient airborne particulate matter into said exhaust skirt and said abrasive blasting helmet, and a respirator face mask adapted for attachment to the face of a person wearing said abrasive blasting helmet, said face mask including an air inlet connector connectable within said barrier to said air outlet port.

19. The air delivery system of claim 6 wherein said neck cuff is constructed of a stretchable, resilient knit material adapted to fit various neck sizes.

20. The air delivery system of claim 6 wherein said air circulating collar is adapted to closely conform to a wearer's neck to provide a barrier to introduction of ambient atmosphere containing particulate matter into a lower end of said exhaust skirt when said air circulating collar is filled with air supplied through said inlet port from a remote source of breathable compressed air.

21. In combination with an abrasive blasting helmet of the type which conventionally includes a dome portion for covering a person's head and a visor containing a cowl portion attached to and around a base of said dome portion and depending from said dome portion so as to cover said person's face, a breathable air delivery and exhalation exhaust system comprising a flexible, air permeable exhalation exhaust skirt open on an upper and a lower end thereof, said exhaust skirt being impermeable to airborne particulate matter associated with abrasive blasting activities, a flexible, cylindrically shaped neck cuff for fitting about a person's neck, one end of said neck cuff being attached to and around an opening defining lower end portion of said exhaust skirt, a hollow, toroidal shaped air circulating collar constructed of a flexible, air impermeable material disposed in and attached to and around a lower end portion of said exhaust skirt, said air circulating collar being adapted to fit comfortably around a person's neck and having an air inlet port and an air outlet port, means for removably attaching an opening defining upper end portion of said exhaust skin to and around said cowl portion, and means for connecting a breathing tube from an external source of breathable compressed air located outside of said exhaust skirt to said air inlet port located within said exhaust skirt.

22. The air delivery system of claim 21 wherein said air inlet port and said air outlet port are located across said air circulating collar from one another, said breathing tube connecting means comprising a hollow sleeve constructed of flexible, air impermeable material connected on one end to said air circulating collar and extending through an opening defining portion of said neck cuff for connection to a breathable compressed air source located external to said exhaust skirt.

23. The air delivery system of claim 21 wherein said air inlet and outlet ports are rotationally spaced apart approximately 180 degrees on said air circulating collar, said air outlet port including a threaded air outlet connector for threadable attachment within said exhaust skirt to an air inlet port of a respirator face mask worn by a person.

24. The air delivery system of claim 21 wherein said exhaust skirt is constructed of woven nylon sail cloth having sufficient porosity to be air and water vapor permeable while being impermeable to airborne particulate matter resulting from abrasive blasting activities.

25. The air delivery system of claim 21 wherein said air circulating collar is constructed of urethane coated woven nylon sail cloth.

26. The air delivery system of claim 21 wherein said neck cuff further comprises an expandable, resilient knit fabric adapted to fit various neck sizes.

27. The air delivery system of claim 26 wherein said knit fabric is selected from the group consisting of wool, polyester and nylon.

28. The air delivery system of claim 21 wherein said connecting means comprises an elongated hollow sleeve constructed of a flexible, air impermeable material which is connected on one end thereof to said air inlet port, said tube extending through said neck cuff under a lower end of said exhaust skirt for connection to a breathable air source located outside of said exhaust skirt.

29. The air delivery system of claim 21 wherein said removably attaching means comprises a raised rib attached to and extending endlessly along a lower edge portion of an interior surface of said cowl portion, a flexible, deformable, resilient circular hoop attached to and around an upper opening defining portion of said exhaust skirt, said circular hoop being adapted to snap over said rib into close fitting compression against the interior surface of said cowl portion above said rib such that said rib acts as a barrier to hold said hoop in said cowl, bracket means attached to said interior surface on one end portion of said abrasive blasting helmet for confining a portion of said hoop therein at a level immediately above and next to said rib, and means attached to and depending from said hoop outside of said exhaust skin for pulling said hoop over said rib and out of said cowl portion to disconnect said exhaust skirt from said abrasive blasting helmet.

30. The air delivery system of claim 29 wherein said bracket means comprises a plurality of downwardly opening L-shaped brackets rotationally spaced from one another and attached on a rear end portion of an interior surface of said abrasion blasting helmet, said pulling means being positionable on a forward end portion of said helmet.

31. The air delivery system of claim 30 wherein said pulling means comprises a flexible strap attached at one end thereof to an upper end portion of said exhaust skirt substantially surrounding said hoop, said strap hanging free outside of said exhaust skirt so that it may be grasped by a person as desired to pull said hoop and exhaust skirt free from attachment to said abrasive blasting helmet.

32. The air delivery system of claim 21 further comprising means for attaching a protective body garment to said abrasive blasting helmet such that said garment covers said exhaust skirt, air circulating collar and neck cuff.

33. The air delivery system of claim 32 wherein said air circulating collar is adapted to closely conform to a person's neck when air is supplied to said air inlet port from a remote source of breathable compressed air to provide a barrier, in cooperation with said exhaust skirt and abrasive blasting helmet, to the introduction of ambient airborne particulate matter into said abrasive blasting helmet.

34. An air delivery and exhalation exhaust system for a protective helmet comprising a flexible, air permeable exhalation exhaust skirt open on an upper and a lower end thereof, said exhaust skirt being impermeable to airborne particulate matter resulting from abrasive blasting activities, means for removably attaching an opening defining upper end portion of said exhaust skirt to and around an interior lower edge portion of a protective helmet, a stretchable, resilient neck cuff adapted to closely conform to and around a wearer's neck, said neck cuff being attached on an upper open end thereof to and around an opening defining lower end portion of said exhaust skirt, and a hollow, toroidal shaped air circulating collar constructed of an air impermeable material disposed in and attached to and around a lower opening defining end portion of said exhaust skirt, said collar containing an air inlet port accessible from outside of said exhaust skirt and an air outlet port accessible from inside of said exhaust skirt, which ports are rotationally spaced apart approximately 180 degrees on said collar, said exhaust skirt, neck cuff and collar together forming a first barrier to introduction of particulate contamination from ambient atmosphere into said protective helmet and into the respiratory system of a wearer thereof when said exhaust skirt is attached to said protective helmet and when said collar is supplied with air from a remote source of breathable compressed air.

35. The system of claim 34 further comprising a respirator face mask having an air inlet connector attached to said collar air outlet port, said face mask forming a second barrier to the introduction of particulate contamination from ambient atmosphere into the respiratory system of a wearer of said protective helmet.

36. The system of claim 35 wherein said protective helmet comprises an abrasive blasting helmet having a dome portion for covering a wearer's head and a cowl portion attached to a base of the dome portion and depending therefrom to cover a wearer's face.

37. The system of claim 35 further comprising a protective body garment having an upper opening adapted for removable connection to and around an exterior lower edge portion of said helmet to enclose said exhaust skirt, neck cuff and collar.

* * * * *

UNITED STATES PATENT AND TRADEMARK OFFICE
CERTIFICATE OF CORRECTION

PATENT NO. : 5,549,104
DATED : Aug. 27, 1996
INVENTOR(S) : Kevin E. Crump, Winchester; Jimmie D. Gard, Sadieville; Richard A. Oleson, Lexington, all of Ky.

It is certified that error appears in the above-indentified patent and that said Letters Patent is hereby corrected as shown below:

Col. 4, line 14,
 "skin" should read --skirt--

Col. 4, line 35,
 "skin" should read --skirt--

Col. 5, line 18,
 "skin" should read --skirt--

Col. 10, line 44, claim 21, "skin" should read --skirt--

Col. 11, line 37, claim 29, "skin" should read --skirt--

Signed and Sealed this

Twenty-ninth Day of October 1996

Attest:

BRUCE LEHMAN

Attesting Officer

Commissioner of Patents and Trademarks